United States Patent [19]

Nussenzweig

[11] Patent Number: 5,171,843
[45] Date of Patent: Dec. 15, 1992

[54] IMMUNOGENIC POLYPEPTIDE AND METHOD FOR PURIFYING IT

[75] Inventor: Victor Nussenzweig, New York, N.Y.

[73] Assignee: New York University, New York, N.Y.

[21] Appl. No.: 175,112

[22] Filed: Mar. 30, 1988

Related U.S. Application Data

[63] Continuation-in-part of Ser. No. 754,645, Jul. 9, 1985, abandoned, which is a continuation-in-part of Ser. No. 115,634, Oct. 26, 1987, Pat. No. 4,915,942, which is a continuation of Ser. No. 649,903, Sep. 12, 1984, Pat. No. 4,690,503.

[51] Int. Cl.$^5$ .......................... C07K 3/00; C07K 13/00
[52] U.S. Cl. .................................. 530/350; 530/416; 424/88
[58] Field of Search ................... 530/350, 416; 424/88

[56] References Cited

PUBLICATIONS

Dame et al, Science, 225(4662), 593–599, 1983.

Primary Examiner—Johann Richter
Attorney, Agent, or Firm—Darby & Darby

[57] ABSTRACT

This invention relates to a synthetic polypeptide (preferably produced by recombinant DNA techniques) comprising an amino acid sequence incorporating (a) a portion of the P.vivax circumsporozoite (CS) protein including the region of the repeat immunodominant epitope of said protein and (b) another portion of such protein which is conserved among the different material species; and to a method for purifying such a polypeptide.

3 Claims, 10 Drawing Sheets

CONSTRUCTION OF A YEAST EXPRESSION PLASMID FOR P.vivax DNA

YEAST EXPRESSION PLASMID pAB24

Western Blot

IEF OF YEAST-ENGINEERED
CS PROTEIN OF *P.vivax* pH  3.86   4.30   5.38   6.64  7.42

FIG. 7

IMMUNOGENIC POLYPEPTIDE AND METHOD FOR PURIFYING IT

This patent application is a continuation-in-part application of copending U.S. patent application Ser. No. 754,645 filed on Jul. 9, 1985, now abandoned in the names of Arnot, D. E. et al, co-pending patent application Ser. No. 115,634, now U.S. Pat. No. 4,915,942 (in turn a Rule 60 continuation of Ser. No. 649,903, filed Sep. 12, 1984) now U.S. Pat. No. 4,690,503 filed Oct. 26, 1987 in the names of Victor Nussenzweig, et al., co-pending PCT application No. US86/01373 filed on Jun. 24, 1986 and co-pending application Ser. No. 32,326 filed in the name of Victor Nussenzweig on Mar. 30, 1987, all assigned to New York University. All of these applications are incorporated by reference herein.

FIELD OF THE INVENTION

This invention relates to an immunogenic polypeptide expressed by a recombinant yeast and comprising an amino acid sequence incorporating a portion of the P. vivax circumsporozoite (CS) protein including the region of the repeat immunodominant epitope of said protein; and to a method for purifying this polypeptide.

The immunogenic properties of the P. vivax CS protein and, in particular, those of a subsequence of this protein have been previously described, in the above-identified Arnot et al application and in Arnot, D. E. et al. Science 230:815-818, 1985 (also incorporated by reference).

In fact, the entire P. vivax CS gene has been identified and its sequence described in the above-mentioned documents. As described therein, the P. vivax CS protein comprises a central region of 19 tandem repeats of the sequence:

Asp-Arg-Ala-Asp/Ala-Gly-Gln-Pro-Ala-Gly or, by another system or notation:

D R A D/A G Q P A G

This region contains the repeat immunodominant epitope of the P. vivax CS protein.

(The correspondence between the two notation systems is as follows: A=alanine, C=cysteine, D=aspartic acid, E=glutamic acid, F=phenylalanine, G=glycine, H=histidine, I=isoleucine, K=lysine, L=leucine, M=methionine, N=asparagine, P=proline, Q=glutamine, R=arginine, S=serine, T=threonine, V=valine, W=tryptophan, and Y=tyrosine.)

Synthetic peptides consisting essentially of 18 amino acid residues (i.e. two repeats of the above repeating sequence and cyclic permutations thereof—such as Asp-Gly-Gln-Pro-Ala-Gly-Asp-Arg-Ala) are recognized by antibodies to the native P. vivax CS protein and in turn generate antibodies (when injected in mammals) which recognize, and bind to, the native CS protein. Hence, such peptides have utility in a vaccine against malaria.

One possible approach to making a vaccine against P. vivax malaria would be to synthesize immunogenic peptides including a sequence corresponding to that of the immunodominant epitope of the P. vivax CS protein (i.e., containing one and preferably two or more repeats). In the case of P. vivax, however, because the sequence of the repeating unit of the CS protein is rather long (in contrast to that of P. falciparum) classical peptide synthesis cannot be reliably used. Use of classical synthetic techniques to make longer peptides is especially inconvenient when practiced on a large scale, as would be necessary for manufacture of a malaria vaccine that would be distributed to millions of people worldwide.

Moreover, coupling of the synthesized peptide to a larger molecule that would play the role of a carrier or adjuvant would be necessary. In addition, in most instances, only a minor proportion of antibodies to a synthetic peptide recognize the same sequence in the native protein. That is, even if the synthetic peptide coupled to a carrier protein is shown to be immunogenic, most of the antibodies produced may not mediate protective immunity against the pathogen. In this respect, the synthetic peptide $(NANP)_3$ which is a candidate for preparing a vaccine against P. falciparum is exceptional, since at least 70% of the antipeptide antibodies recognize the malaria sporozoites. The explanation for this unusual finding is probably that the $(NANP)_3$ peptide contains many prolines (P) and asparagines (N), amino acids which are frequently found in reverse turns of the protein molecule. Perhaps in this instance, a preferred configuration of $(NANP)_3$ in solution, mimics that of the same sequence in the native CS protein. However, from the examination of the amino acid sequence of the P. vivax repeats, it does not seem likely that a P. vivax peptide will behave similarly to $(NANP)_3$.

For these reasons, an alternative technique was sought for manufacturing an immunogenic peptide that could be used in a vaccine against P. vivax malaria. The present inventors looked to recombinant DNA and genetic engineering techniques to express immunogenic polypeptides that would be used to confer immunity to mammals against P. vivax malaria.

Although the technology was readily available for constructing recombinant bacteria that would express a portion or all of the repeating amino acid sequence of the P. vivax protein, the present inventors searched for an alternative expression system for the following reasons:

First, the expression system should be reliable and able to produce the polypeptide of interest consistently and with a high yield. Bacteria can be difficult to handle when produced in mass culture and overexpressing a foreign protein product.

Second, and more important, expression products of bacteria are often difficult to purify from pyrogenic impurities and other inflammatory and toxic agents that either are co-expressed by the bacteria, or are necessary additives in a bacterial growth medium.

Third, expression products of bacteria are most often fusion proteins, that is, they contain additional non-relevant sequences originating from the genes associated with the bacteria.

The present inventors looked to yeast expression systems, which have been substantially improved by recent advances in the field of recombinant DNA technology. Yeasts are hardier organisms than bacteria and much easier to grow in mass culture. Moreover, recent advances in yeast genetics and cloning have increased the yields of yeast expression systems.

Purification of expression products of recombinant yeast systems is not a priori more complicated than purification of products of bacterial recombinant systems and depends mostly on the characteristics of the particular protein sought to be purified Nevertheless, such purification is generally more complicated than that of a peptide or protein produced by classical peptide synthetic techniques.

The present inventors chose a general yeast expression system that is the subject matter of U.S. patent application Ser. No. 868,639 filed on May 29, 1986 in the name of R. L. Burke et al and assigned to Chiron Corporation. This application is incorporated by reference herein. A portion of the *P. vivax* gene was chosen (for incorporation into the yeast organisms) which included the entire tandemly repeated sequence plus another segment preceding the repeat region (when the sequence is read from the N-terminal to the C-terminal). This segment incorporates a sequence that is highly conserved in all malarial species and has been previously found to be immunogenic in its own right. (See U.S. patent application Ser. No. 649,903 of V. Nussenzweig et al filed on Sep. 18, 1984 (now issued as U.S. Pat. No. 4,915,942) assigned to New York University and incorporated by reference herein.)

OBJECTS OF THE INVENTION

Accordingly, it is an object of the present invention to provide an immunogenic yeast-engineered polypeptide immunochemically reactive with monoclonal antibodies against *P. vivax* circumsporozoite (CS) protein, and useful in a vaccine preparation against malaria.

It is another object of the present invention to provide a method for making the foregoing immunogenic polypeptide which could be practiced on a large scale and with a high yield.

Another object is to provide an immunogenic polypeptide suitable for incorporation in an anti-malaria vaccine preparation.

Another object is to provide an immunogenic polypeptide suitable for use in an anti-malaria vaccine preparation without being coupled to a carrier.

Another object is to provide a method for purifying the foregoing yeast-engineered polypeptide from an impure preparation thereof comprising lysed yeast cell material and yeast culture media.

These and other objects of the invention will be apparent to those skilled in the art in view of the present specification, accompanying claims and appended drawings.

BRIEF DESCRIPTION OF THE DRAWINGS

FIG. 7 is a radioautograph of an isoelectric focusing gel showing the engineered polypeptide of the present invention.

SUMMARY OF THE INVENTION

Figure 1:
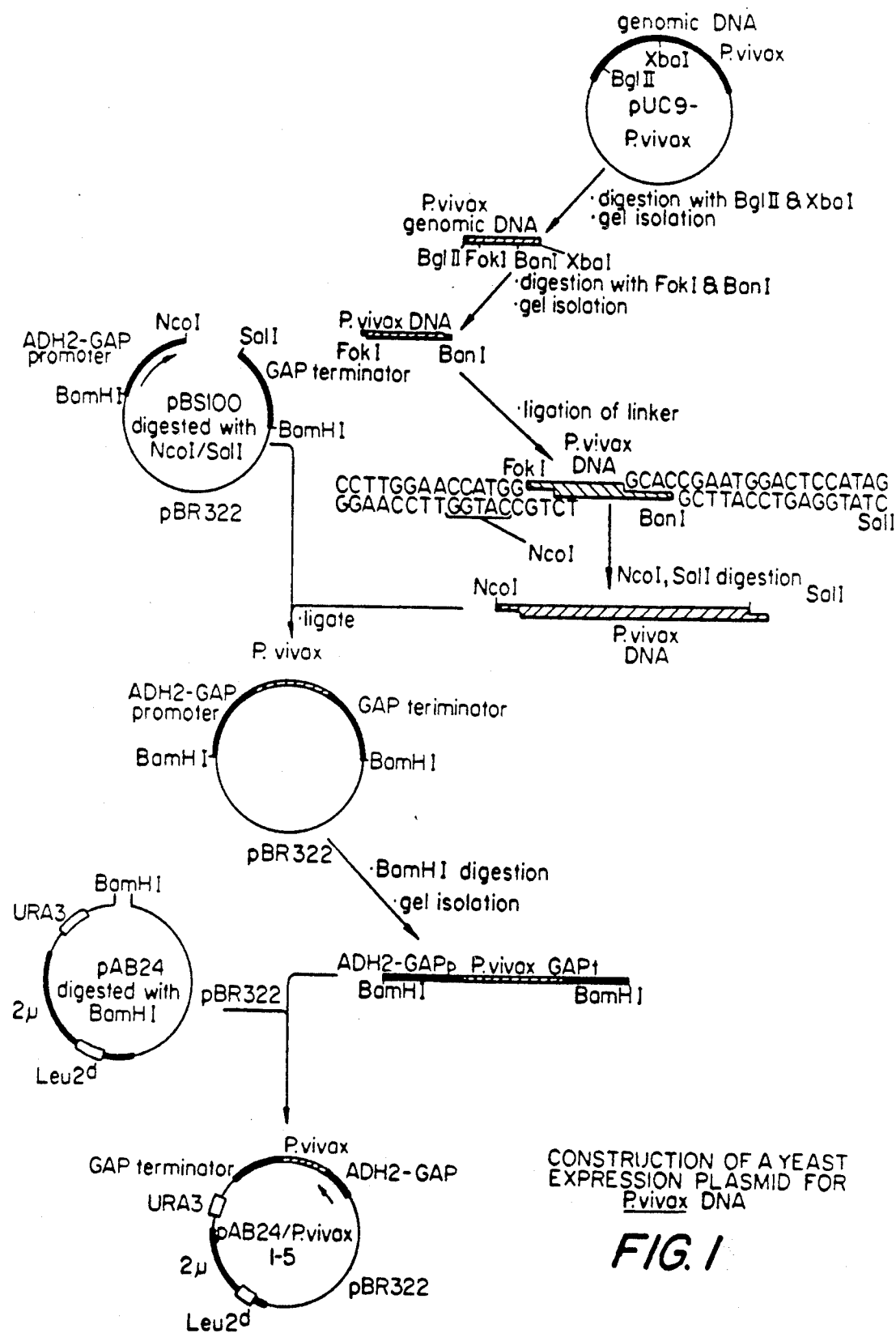
FIG. 1 is a diagram of the construction of the yeast expression vector used in the present invention.

This invention relates to a yeast-engineered polypeptide having an amino acid sequence consisting essentially of the amino acid sequence:

A E P K N P R E N K L K Q P G D R A D G Q P A G D R A D G

Q P A G D R A D G Q P A G D R A A G Q P A G D R A D G Q P

A G D R A D G Q P A G D R A D G Q P A G D R A D G Q P A G

D R A A G Q P A G D R A A G Q P A G D R A D G Q P A G D R

A A G Q P A G D R A D G Q P A G D R A A G Q P A G D R A D

G Q P A G D R A A G Q P A G D R A A G Q P A G D R A A G Q

P A G D R A A G Q P A G N G A G G Q A A G G N A G G Q G Q

N N E G A N A P N E K S V K E Y L D K V R A T V G T E W T

P and produced by a method comprising the steps of:
(a) obtaining a 15 kilobase restriction endonuclease Bgl II *P. vivax* CS DNA fragment in a suitable vector;
(b) subcloning said fragment in a suitable vector;
(c) obtaining a 4.1 kilobase *P. vivax* DNA fragment coding for said amino acid sequence;
(d) incorporating said fragment into a yeast expression vector,
(e) transforming yeast with said expression vector,
(f) culturing said yeast under conditions which allow expression of the protein encoded by said vector, and
(g) harvesting the medium containing said expressed protein.

DETAILED DESCRIPTION OF THE INVENTION

The *P. vivax* CS gene is set forth below (together with the amino acid sequence for which it codes)

[N-terminus] ATGAAGAACTTCATTCTCTTGGCTGTTTCTTCCATCCTGTTGGTGGACTTG
           M  K  N  F  I  L  L  A  V  S  S  I  L  L  V  D  L TTCCCCACGCACTGCGGGCACAATGTAGATCTGTCCAAGGCCATAAACTTAAATGGAGTAAAC
 F  P  T  H  C  G  H  N  V  D  L  S  K  A  I  N  L  N  G  V  N TTCAATAATGTAGACGCCAGTTCACTTGGCGCGGCACACGTAGTAGGACAAAGTGCTAGCCGAGGCAG
 F  N  N  V  D  A  S  S  L  G  A  A  H  V  V  G  Q  S  A  S  R  G  R AGGCCTTGGCGAGAACCCAGATGACGAGGAAGGAGATGCTAAAAAAAAAAAGGATGGAAAGAAA
  G  L  G  E  N  P  D  D  E  E  G  D  A  K  K  K  K  D  G  K  K GCAGAACCAAAAAATCCACGTGAAAATAAGCTGAAGCAACCAGGAGACAGAGCAGATGGACAGC
 A  E  P. K  N  P  R  E  N  K  L  K  Q  P  G  D  R  A  D  G  Q CAGCAGGAGACAGAGCAGATGGACAGCCAGCAGGTGATAGAGCAGATGGACAACCAGCAGGAGA
 P  A  G  D  R  A  D  G  Q  P  A  G  D  R  A  D  G  Q  P  A  G  D TAGAGCAGCTGGACAACCAGCAGGAGATAGAGCAGATGGACAGCCAGCAGGAGACAGAGCAGAT
  R  A  A  G  Q  P  A  G  D  R  A  D  G  Q  P  A  G  D  R  A  D GGACAGCCAGCAGGAGACAGAGCAGATGGACAACCAGCAGGAGACAGAGCAGATGGACAACCAG
 G  Q  P  A  G  D  R  A  D  G  Q  P  A  G  D  R  A  D  G  Q  P CAGGTGATAGAGCAGCTGGACAACCAGCAGGTGATAGAGCAGCTGGACAACCAGCAGGAGATAG
 A  G  D  R  A  A  G  Q  P  A  G  D  R  A  A  G  Q  P  A  G  D  R AGCAGATGGACAGCCAGCAGGAGATAGAGCAGCTGGACAGCCAGCAGGAGATAGAGCAGATGGA
  A  D  G  Q  P  A  G  D  R  A  A  G  Q  P  A  G  D  R  A  D  G CAGCCAGCAGGAGATAGAGCAGCTGGACAGCCAGCAGGAGATAGAGCAGATGGACAGCCAGCAG
 Q  P  A  G  D  R  A  A  G  Q  P  A  G  D  R  A  D  G  Q  P  A GAGATAGAGCAGCTGGACAGCCAGCAGGAGATAGAGCAGCTGGACAGCCAGCAGGAGATAGAGC
 G  D  R  A  A  G  Q  P  A  G  D  R  A  A  G  Q  P  A  G  D  R  A AGCTGGACAGCCAGCAGGAGATAGAGCAGCTGGACAGCCAGCAGGAAATGGTGCAGGTGGACAG
  A  G  Q  P  A  G  D  R  A  A  G  Q  P  A  G  N  G  A  G  G  Q GCAGCAGGAGGAAACGCAGGAGGACAGGGACAAAATAATGAAGGTGCGAATGCCCCAAATG
 A  A  G  G  N  A  G  G  Q  G  Q  N  N  E  G  A  N  A  P  N GAAAGTCTGTGAAAGAATACCTAGATAAAGTTAGAGCTACCGTTGGCACCGAATGGACTCCATG
 E  K  S  V  K  E  Y  L  D  K  V  R  A  T  V  G  T  E  W  T  P  C CAGTGTAACCTGTGGAGTGGGTGTAAGAGTCAGAAGCAGAGTTAATGCAGCTAACAAAAAACCA
  S  V  T  C  G  V  G  V  R  V  R  S  R  V  N  A  A  N  K  K  P GAGGATCTTACTTTGAATGACCTTGAGACTGATGTTTGTACAATGGATAAGTGTGCTGGCATAT
 E  D  L  T  L  N  D  L  E  T  D  V  C  T  M  D  K  C  A  G  I TTAACGTTGTGAGTAATTCATTAGGGCTAGTCATATTGTTAGTCCTAGCATTATTCAATTAA
 F  N  V  V  S  N  S  L  G  L  V  I  L  L  V  L  A  L  F  N

[C-terminus]

The DNA fragment chosen for insertion in the yeast host was:

GCAGAACCAAAAAATCCACGTGAAAATAAGCTGAAGCAACCAGGAGACAGAGCAGATGGACAGC
 A  E  P  K  N  P  R  E  N  K  L  K  Q  P  G  D  R  A  D  G  Q

CAGCAGGAGACAGAGCAGATGGACAGCCAGCAGGTGATAGAGCAGATGGACAACCAGCAGGAGA
 P  A  G  D  R  A  D  G  Q  P  A  G  D  R  A  D  G  Q  P  A  G  D

TAGAGCAGCTGGACAACCAGCAGGAGATAGAGCAGATGGACAGCCAGCAGGAGACAGAGCAGAT
  R  A  A  G  Q  P  A  G  D  R  A  D  G  Q  P  A  G  D  R  A  D

GGACAGCCAGCAGGAGACAGAGCAGATGGACAACCAGCAGGAGACAGAGCAGATGGACAACCAG
 G  Q  P  A  G  D  R  A  D  G  Q  P  A  G  D  R  A  D  G  Q  P

CAGGTGATAGAGCAGCTGGACAACCAGCAGGTGATAGAGCAGCTGGACAACCAGCAGGAGATAG
 A  G  D  R  A  A  G  Q  P  A  G  D  R  A  A  G  Q  P  A  G  D  R

AGCAGATGGACAGCCAGCAGGAGATAGAGCAGCTGGACAGCCAGCAGGAGATAGAGCAGATGGA
  A  D  G  Q  P  A  G  D  R  A  A  G  Q  P  A  G  D  R  A  D  G

CAGCCAGCAGGAGATAGAGCAGCTGGACAGCCAGCAGGAGATAGAGCAGATGGACAGCCAGCAG
 Q  P  A  G  D  R  A  A  G  Q  P  A  G  D  R  A  D  G  Q  P  A

GAGATAGAGCAGCTGGACAGCCAGCAGGAGATAGAGCAGCTGGACAGCCAGCAGGAGATAGAGC
 G  D  R  A  A  G  Q  P  A  G  D  R  A  A  G  Q  P  A  G  D  R  A

```
AGCTGGACAGCCAGCAGGAGATAGAGCAGCTGGACAGCCAGCAGGAAATGGTGCAGGTGGACAG
  A   G   Q   P   A   G   D   R   A   A   G   Q   P   A   G   N   G   A   G   G   Q

GCAGCAGGAGGAAACGCAGGAGGACAGGGACAAAATAATGAAGGTGCGAATGCCCCAAATG
  A   A   G   G   N   A   G   G   Q   G   Q   N   N   E   G   A   N   A   P   N

AAAAGTCTGTGAAAGAATACCTAGATAAAGTTAGAGCTACCGTTGGCACCGAATGGACTCCA
  E   K   S   V   K   E   Y   L   D   K   V   R   A   T   V   G   T   E   W   T   P
```

This fragment includes the entire tandem repeat sequence plus a region that is substantially parallel to Region I of Dame, et al Science 225:628 (1984), precedes the repeat region, and codes for the amino acid sequence A E P K N P R E N K L K Q P G.

This sequence includes the subsequence K L K Q P which is conserved in all malarial species that have been investigated to date.

The foregoing DNA fragment was obtained from the entire gene by subcloning a 15 kb BglII fragment isolated as described by Arnot et. al (U.S. patent application Ser. No. 754,645, and Science 230:815-818, Nov. 15, 1985) both incorporated by reference. It was then inserted in the DNA of modified yeast plasmid pAB24 as described in Example 1 below.

For expression of the P. vivax CS antigen in yeast, a hybrid promoter comprising the strong yeast glyceraldehyde-3-phosphate dehydrogenase and the glucose regulatable alcohol dehydrogenase-2 (ADH-2) promoter was used. Fusion of this promoter to heterologous genes allows the growth of yeast cultures to high density using glucose as a carbon source. Depletion of glucose in the media during fermentative growth leads to concomitant induction of expression of the heterologous protein. Incorporation of the plasmid into high copy number, autonomously replicating yeast plasmids, and transformation of yeast cells generated strains capable of expressing high levels of CS proteins on induction.

The yeast was grown in culture in YEP medium (1% w/v yeast extract, 2% peptone) with 1% glucose as described in Example 1 below. Two hundred liters of yeast material were thus obtained and stored at −80° C.

The thus obtained yeast material contained a complex mixture of different yeast proteins as well as culture medium additives. Gel electrophoresis of this material on 7.5% sodium dodecyl sulfate polyacrylamide gel gave an indication of its heterogeneity (see FIG. 6, lane 1). The expression procedure and plasmid construction are outlined in FIG. 1 and described in Example 1, below.

It had been observed that all antibodies to the P. knowlesi CS protein recognized the immunodominant epitope region of this protein even after the CS protein had been heated at 100° C. for 30 minutes or subjected to complete denaturation by treatment with 6M guanidine and 1% betamercaptoethanol (Gysin, J., et al J. Exp. Med. 160:935, 1984; Godson, G. N., et al Nature 305:29, 1983).

This observation concerned the entire P. knowlesi CS protein and by no means established either that the P. vivax CS protein would show similar behavior upon heating or that fragments thereof, consisting essentially of the polypeptide employed herein and encompassing the epitope region, would continue to be immunochemically reactive with anti-P. vivax CS protein antibodies, after being subjected to heating conditions that normally result in denaturation of proteins. Another imponderable was that, in the present invention, the fragment of the CS protein was mixed with very large amounts of nonrelevant materials. Heating of the mixture might lead to the formulation of aggregates with other polypeptides and masking of the epitopes and/or coprecipitation. It was also not known whether such fragments would continue to be immunogenic after being subjected to the above heating treatment.

Nevertheless, the present inventors used a heating step as the initial step in the purification of the yeast-engineered P. vivax CS polypeptide. (As used in this patent application, "polypeptide" will refer to a relatively long protein fragment, "protein" will refer to the entire protein, and "peptide" will refer to a relatively short peptide, e.g., one containing 30 amino acid residues or less. Regarding the use of the word "sequence", it will be understood that polypeptides and peptides in accordance with the present invention will be functionally equivalent if they have the same sequence whether the sequence is set forth from the N to the C terminus or from the C to the N terminus).

The mixture was then subjected to heating at 100° C., which resulted in massive precipitation of lysed yeast cell material. The supernatant was separated, dried and lyophilized. The lyophilized supernatant residue showed a substantial improvement in purity over the yeast extract (see FIG. 6, lane 4).

A solution of the lyophilized material was then further purified sequentially by (a) anion-exchange chromatography using an electrolyte gradient to elute the engineered CS polypeptide; and (b) molecular sieve chromatography.

The fractions containing CS polypeptide activity were identified with a radioimmunoassay. A small amount of the highly purified yeast material was radiolabelled to a high specific activity with $^{125}$I. Each fraction was assayed by a classical radioimmunoassay for its capacity to inhibit the binding of the labelled material to immobilized anti-P. vivax monoclonal antibody, directed against the repetitive epitope of the P. vivax CS protein.

A major advantage of the purification process of the present invention is its simplicity and its ready adaptability to scale-up. The thus purified engineered P. vivax CS polypeptide is homogeneous by SDS-PAGE and isoelectric focusing and is thus expected to be substantially free of pyrogenic, inflammatory and toxic impurities that may have been associated with the lysed yeast cell material and yeast culture media.

The yield of the combination of the yeast expression procedure and the purification process of the present invention proved to be 13 mg of pure CS polypeptide per liter of yeast culture. Given that 200 liters of this culture were produced in three days using pilot scale equipment (250 liter fermenter), it is apparent that large amounts of the engineered CS polypeptide can be made available in a short period of time.

A 200-liter stock of yeast extract contains sufficient engineered CS polypeptide to immunize about 25,000 humans against *P. vivax*, using 100 micrograms of polypeptide per person.

Major advantages of the CS polypeptide produced in accordance with the present invention include that the engineered peptide:

(a) can be produced in large scale free of impurities and of non-relevant antigens;
(b) represents a large fragment of the native CS molecule;
(c) has been shown to be highly immunogenic in rodents using aluminum hydroxide as an adjuvant;
(d) the antibodies which are produced react with both the "repeats" and a conserved region of the CS molecule.

Antibodies to the "repeats" have been shown to neutralize parasite injectivity very effectively. Antibodies to a peptide containing this conserved region also neutralized parasite injectivity, but the inhibitory activity could not be accurately quantitated (Vergara, et al, *J. Immunol.* 134: 3445-3448, 1985). Moreover, the fact that the sequence KLKQP, which is part of the peptide, is present in all CS proteins, suggests that this region has an important function.

The present invention is described in detail below by specific examples which are intended to illustrate the invention without limiting its scope.

EXAMPLE 1

Restriction of the *P. vivax* CS gene, Ligation into a Vector, Transformation of the Host Yeast Cells and Expression In the following description all restriction endonucleases and enzymes are commercially available from Pharmacia Fine Chemical Co., (Piscataway, N.J.), New England Biolabs (Beverley, Mass.), Boehringer Mannheim (Indianapolis, Ind.) or Bethesda Research Laboratories, Inc. (Gaithersburg, Md.) and are used according to the manufacturer's instruction.

A pUC9 vector (Pharmacia Fine Chemical Co., Piscataway, N.J.) containing the *P. vivax* CS protein gene, was derived by subcloning a 15-kb BglII fragment inserted into the BamHI sites of EMBL3, a bacteriophage lambda vector (as disclosed in Arnot et. al., U.S. Pat. application Ser. No. 754,645 incorporated by reference). Clone pUC9Ci was digested with BglII and XBaI and gel-purified to obtain a 4.1 kb fragment encoding all the repeat sequences (Arnot et. al., *Science* 230: 815–818, 1985, incorporated by reference.). This gel-purified fragment was then digested with FokI and BanI and ligated to the following 5'-phosphorylated synthetic linkers synthesized by phosphoramidite method using Applied Biosystems' 380A DNA synthesizers.

I CCTTGGAACCATGG
   GGAACCTTGGTACCGTCT
                   NcoI  Complementary to FokI overhang

II GCACCGAATGGACTCCATAG
      GCTTACCTGAGGTATCCAGCT

BanI                       SalI

Linker I provides for an NcoI site, while Linker II provides a SalI overhang.

The linker-containing fragment was digested with NcoI and SalI, isolated by gel electrophoresis and cloned onto NcoI/SalI digested pBS100 (construction described below). The resulting plasmid is designated pAG/*P. vivax*1. pBS100 is a pBR322-derived plasmid containing the ADH-2 regulated GAPDH (glyceraldehyde-3-phosphate dehydrogenase) promoter (1200 bp) and GAPDH terminator (900 bp) (See FIG. 1) and its construction is described below.

The ADH-2 portion of the promoter was constructed by cutting a plasmid containing the wild type ADH-2 gene (plasmid pADR2, see Beier and Young, *Nature*, 300: 724–728 (1982) incorporated by reference with the restriction enzyme EcoR5, which cuts at a position +66 relative to the ATG start codon, as well as in two other sites in pADR2, outside of the ADH-2 region. The resulting mixture of a vector fragment and two smaller fragments was digested with Bal31 exonuclease to remove about 300 bp. Synthetic XhoI linkers having the sequence

CCTCGAGG

GGAGCTCC were chemically synthesized and ligated onto the Bal31 treated DNA. The resulting DNA linker vector fragment (about 5 kb) was separated from the linkers by column chromatography (on Sepharose CL4B from Pharmacia), cut with the restriction enzyme XhoI, religated and used to transform *E. coli* to ampicillin resistance. The positions of the XhoI linker additions were determined by DNA sequencing using standard techniques well known in the art. One plasmid which contained an XhoI linker located within the 5' non-transcribed region of the ADH-2 gene (position −232 from ATG) was cut with the restriction enzyme XhoI, treated with single-strand specific nuclease S1, and subsequently treated with the restriction enzyme EcoRI to create a linear vector molecule having one blunt end at the site of the XhoI linker and an EcoRI end.

The GAP portion of the promoter was constructed by cutting plasmid pPGAP (as disclosed in European patent application No. 164,666 of Chiron Corporation incorporated by reference and filed May 3, 1988 and corresponding to U.S. patent application Ser. No. 609,540, incorporated by reference, filed on May 11, 1984, also owned by Chiron Corporation now U.S. Pat. No. 4,876,197) with the enzymes BamHI and EcoRI, followed by the isolation of the 0.4 Kbp DNA fragment. Plasmid pPGAP is a yeast plasmid containing a yeast GAPDH promoter and terminator sequences with flanking NcoI and SalI restriction endonuclease sites. The purified fragment was partially digested with the enzyme AluI to create a blunt end near the BamHI site and used to construct plasmid pJS104.

Plasmid pJS104 was constructed by the ligation of the AluI-EcoRI GAP promoter fragment to the ADH-2 fragment present on the linear vector described above.

The BamHI-NcoI ADH-GAP promoter fragment was obtained from plasmid pJS103, which is the same as pJS104 (supra) except that the GAP fragment of the ADH-GAP promoter is about 200 bp in pJS103 and 400 bp in pJS104. Construction of pJS103 was the same as that for pJS104 except that the 0.4 kb BamHI-EcoRI fragment was completely digested with AluI (instead of partially digested for pJS104) and a 200 bp fragment was isolated.

Figure 2:
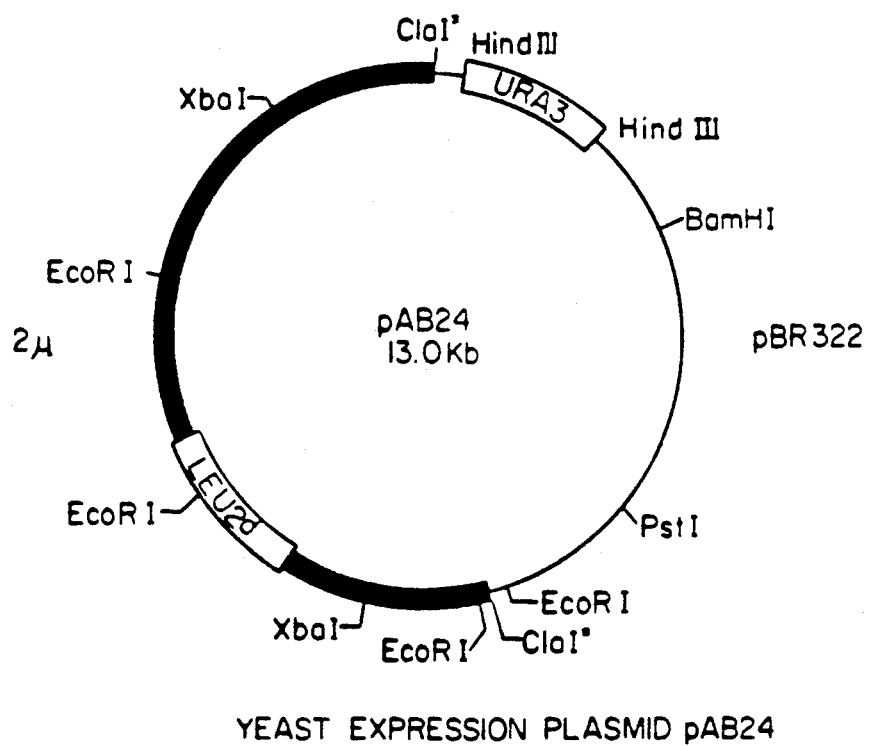
FIG. 2 is a map of yeast plasmid pAB24.
Figure 3:
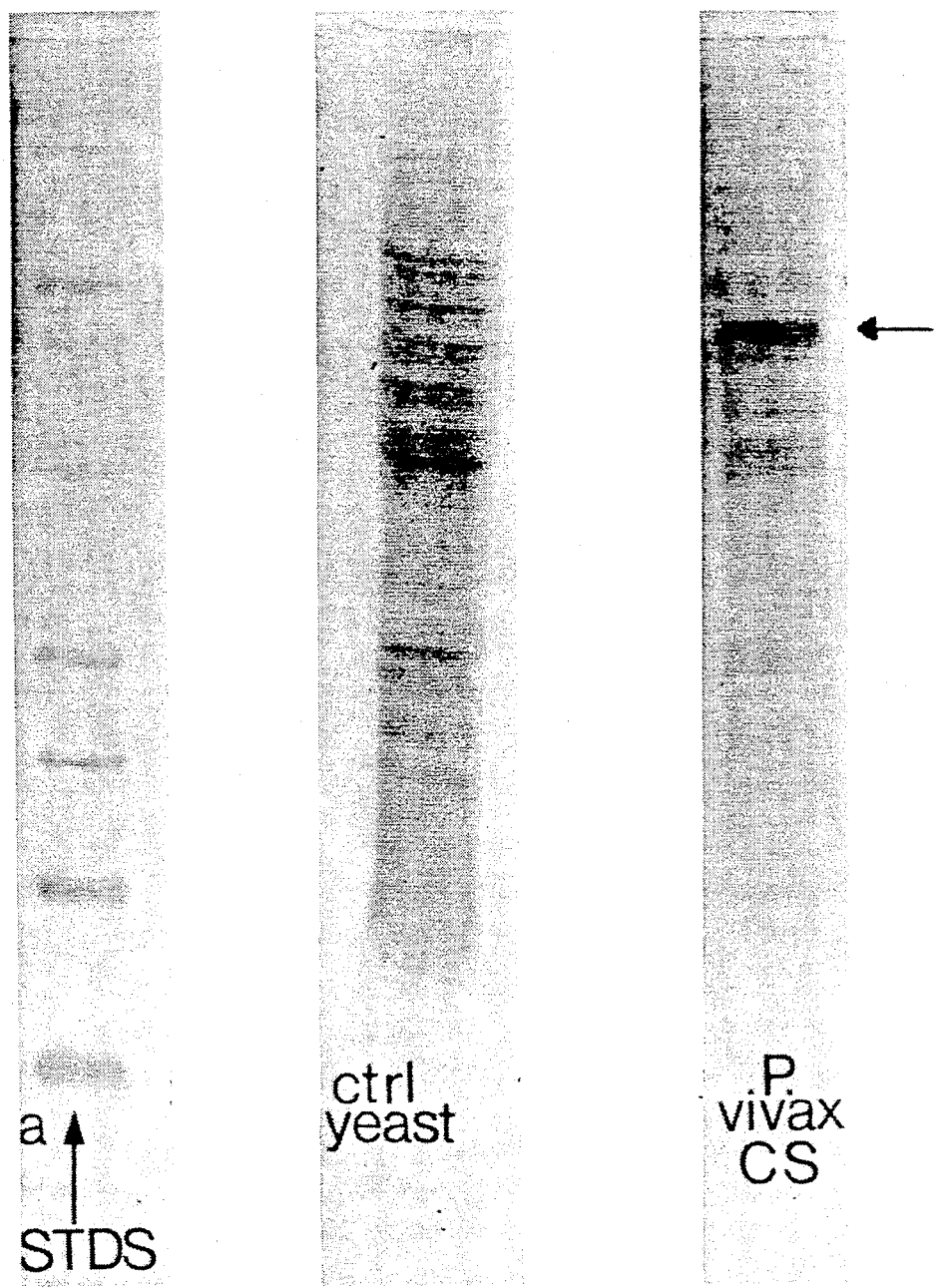
FIG. 3 is a polyacrylamide gel obtained using lysates from *P. vivax*/pAB24-transformed yeast and control yeast.
Figure 4:
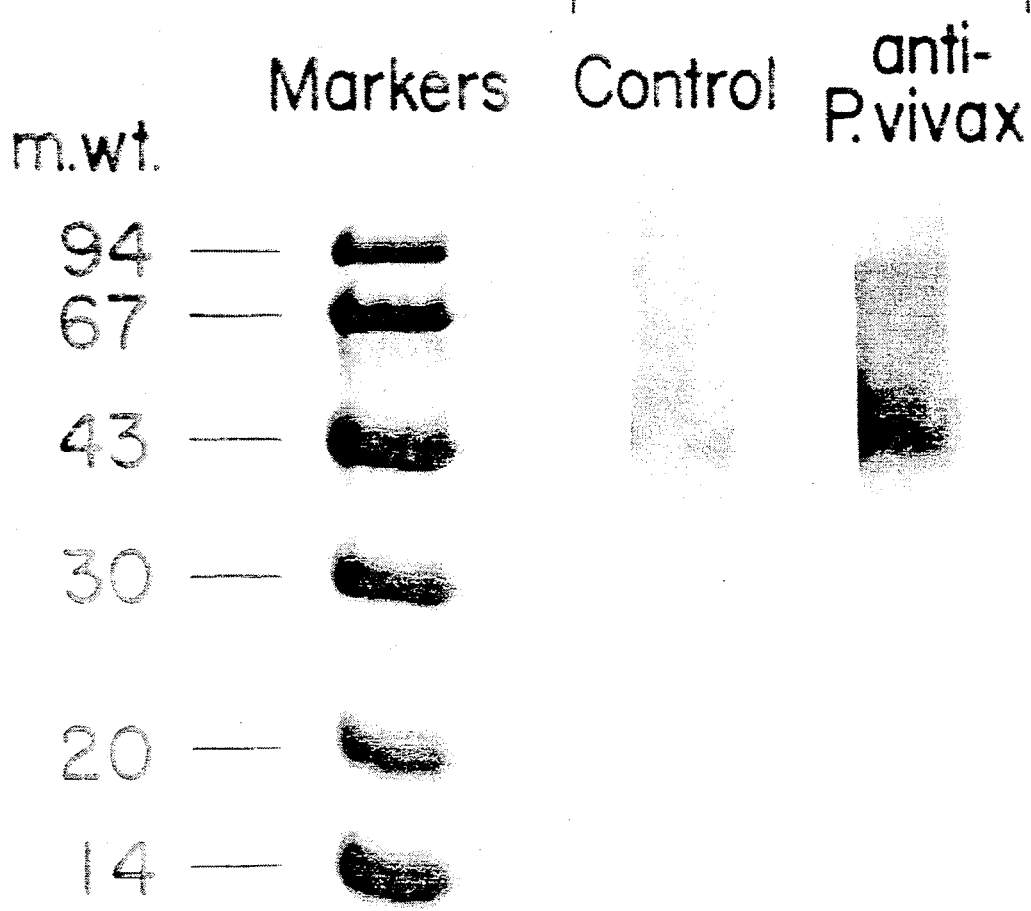
FIG. 4 is a Western analysis of lysates from yeast transformed with the *P. vivax*/pAB24 vector.
Figure 5:
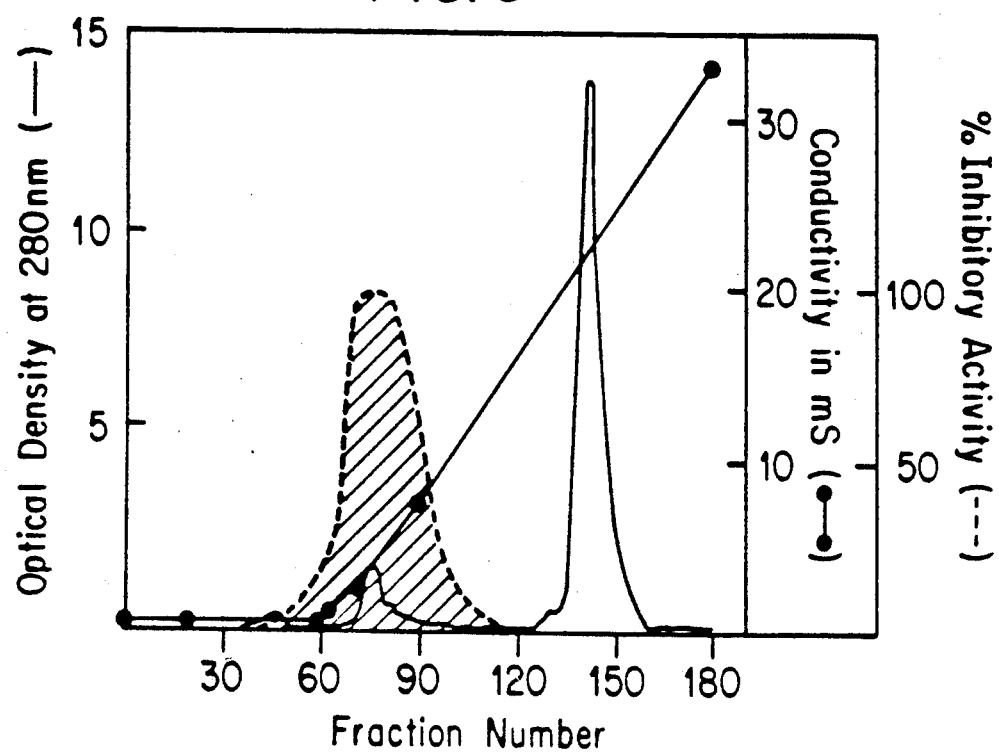
FIG. 5 is a plot of (a) the optical density profile of the material purified according to the invention (solid line); (b) the conductivity of the eluting buffer (solid line-black points); and (c) the percent activity of eluted fractions in inhibiting the binding of antibody to native CS protein.

The entire above region containing the promoter, *P. vivax* segment and terminator, (hereinafter termed the "expression cassette") was excised by digestion with BamHI, purified by gel electrophoresis and cloned into BamHI-digested pAB24. A restriction map of this plasmid is shown in FIG. 2.

pAB24 is a yeast expression vector (FIG. 2) which contains the complete 2 mu sequences necessary for an autonomous replication in yeast (Broach, in: *Molecular Biology of the Yeast Saccharomyces*, 1:445, Cold Spring Harbor Press, 1981) and pBR322 sequences. It also contains the yeast URA3 gene derived from plasmid YEp24 (Botstein, et al., *Gene* (1979) 8:17 incorporated by reference) and the yeast LEU2$^d$ gene derived from plasmid pCl/l European patent application No. 116,201 filed Aug. 22, 1984 by Chiron Corporation and corresponding to U.S. patent application Ser. No. 81302 filed on Aug. 3, 1987 now U.S. Pat. No. 4,870,008, which matured from Ser. No. 81302 filed on Aug. 3, 1987 is a continuation-in-part of the 1983 application. Insertion of the expression cassette was in the BamHI site of pBR322, thus interrupting the gene for bacterial Resistance to tetracyclin.

Figure 6:
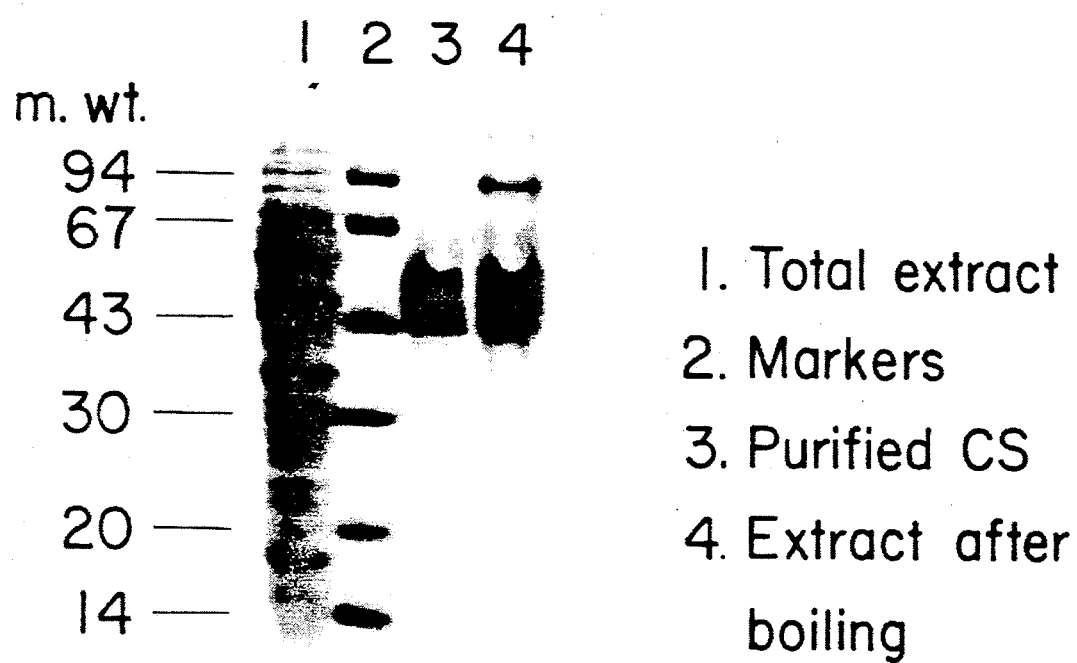
FIG. 6 is a radioautograph of a SDS-PAGE gel demonstrating the purity of the engineered polypeptide when made and purified in accordance with the present invention.
Figure 8:
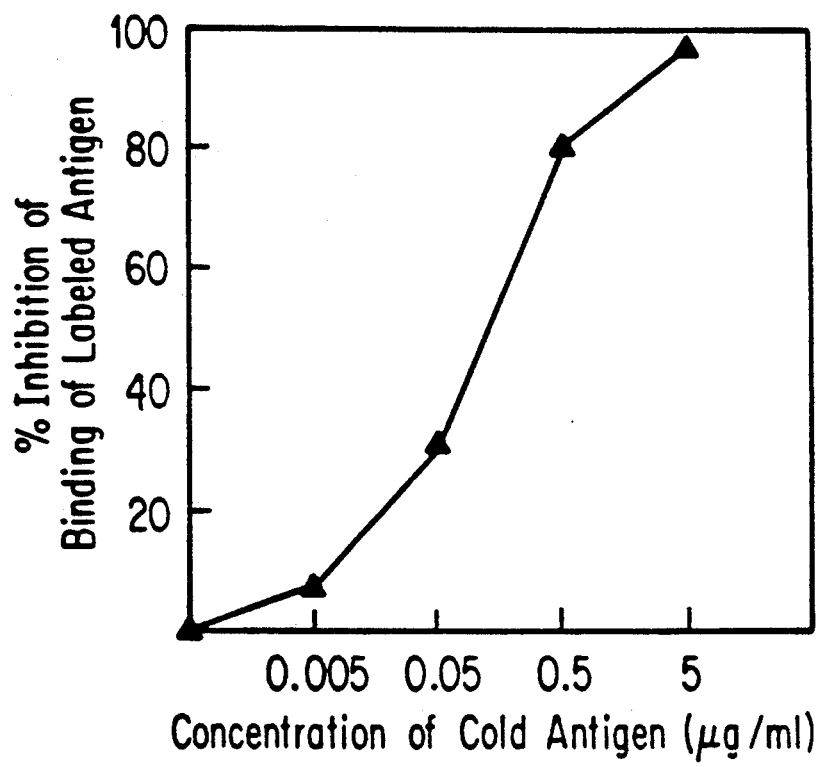
FIG. 8 is a standard curve for a competitive radioimmunoassay and shows the inhibition of binding of labeled, engineered CS polypeptide to anti-vivax CS protein antibodies by the presence of unlabeled engineered polypeptide of the present invention.
Figure 9:
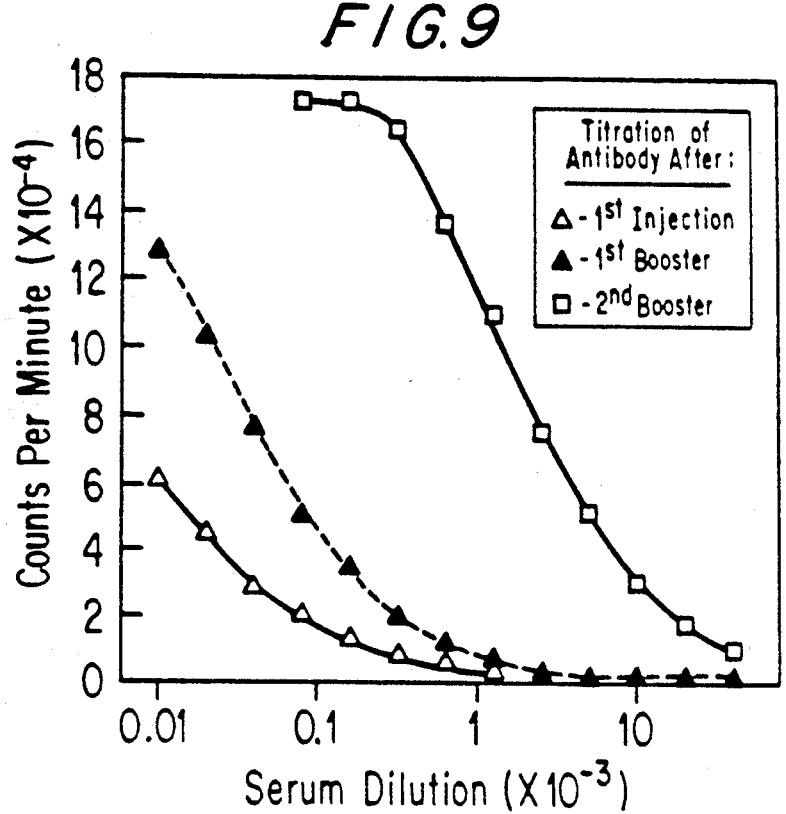
FIG. 9 is a plot of the amount of radiolabeled goat anti-mouse IgG recognizing mouse antisera bound to engineered CS polypeptide, as a function of the mouse serum dilution.
Figure 10:
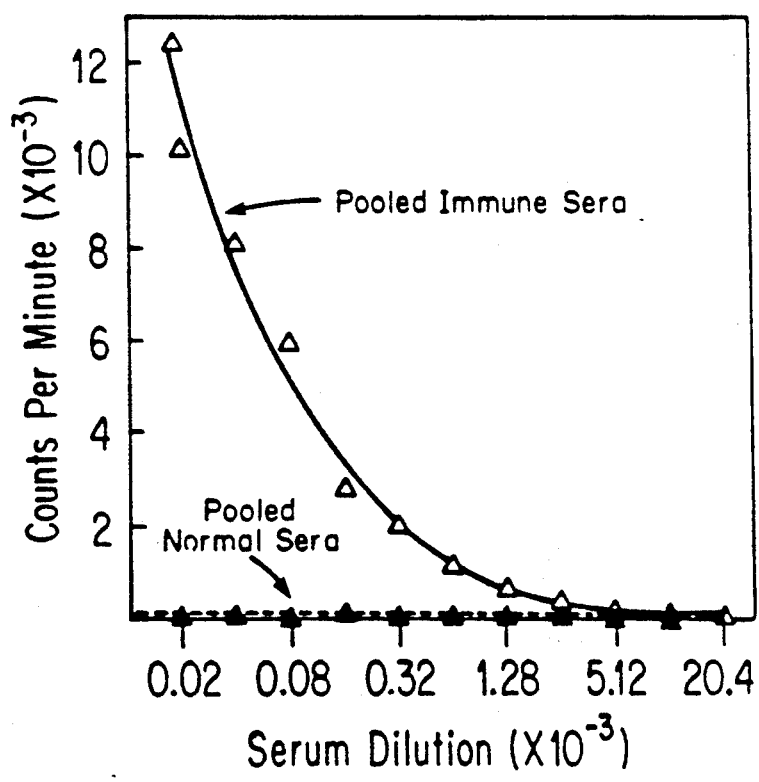
FIG. 10 is a plot of the binding of labeled mouse antisera (raised against the engineered peptide) to immobilized synthetic 18-amino acid (repeat) vivax CS peptide, as a function of the antibody concentration.
Figure 11:
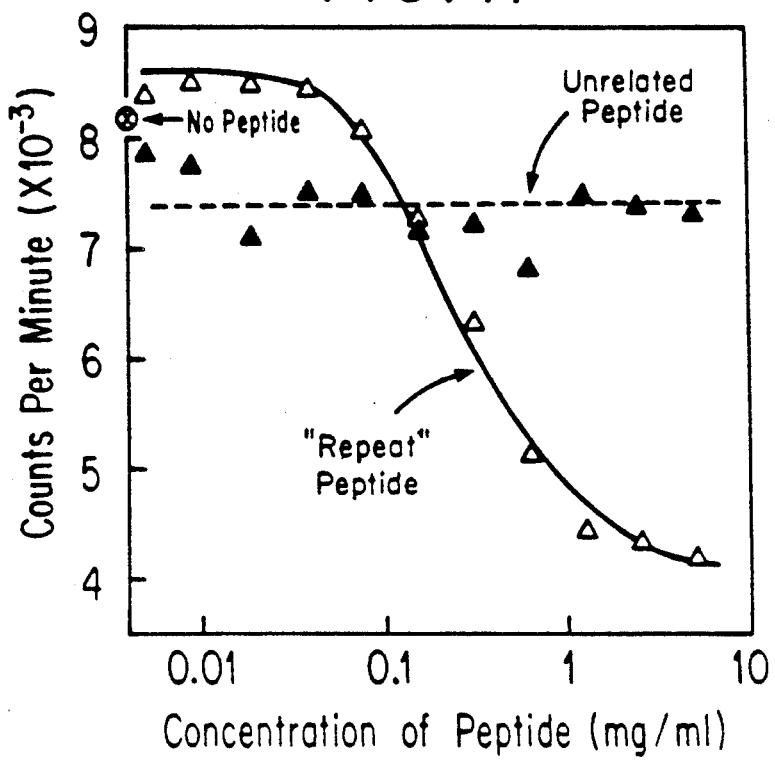
FIG. 11 is a plot of the inhibition by synthetic vivax CS repeat peptide of the binding of mouse antisera to immobilized engineered CS polypeptide prepared and purified according to the present invention, as a function of the concentration of the synthetic (inhibiting) peptide.

Expression of *P. vivax* CS proteins

*Saccharomyces cerevisiae* strain AB110 isolated by Chiron Corporation (Mat, leu2-04, or both leu2-3 and leu2-112, pep4-3, his4-580, cir°) was transformed with pAB24/*P. vivax*1-5 according to Hinnen, et al., *Proc. Natl. Acad. Sci. U.S.A.* 75:1929–1933 (1978). Single-transformant colonies harboring GAP-regulated vectors were grown in 2 ml of leu$^-$ (leucine-depleted) selective media to late log or stationary phase. Only yeast harboring the plasmid can grow in this medium. Cultures were subsequently diluted 1:20 (v/v) in YEP (1% w/v yeast extract, 2% w/v peptone) with 1% glucose, and grown to saturation (about 36 h) in this medium. Cells were lysed in the presence of sodium dodecyl sulfate (SDS) and dithiothreitol (DTT) and the lysates were clarified by centrifugation. Cleared lysates were subjected to polyacrylamide gel electrophoresis (Laemmli, U.K., *Nature*, 277:680, 1970). Following staining with Coomassie blue, a heavy band of about 38 kD was observed in extracts from transformants containing the *P. vivax* plasmid (FIG. 3). This band was detected in those cells transformed with the expression vector, while being absent from extracts of cells harboring control (pCl/l) plasmids. The fusion protein accounts for over 10% of the total cell protein. The reason for abnormal cell migration (38 kD versus 23 kD, predicted from DNA construction) may be attributable to anomalous SDS binding as previously reported for *P. knowlesi* CS proteins (Ozaki, et al., Cell 34:185, 1983), probably due to the low proportion of hydrophobic residues.

To confirm the identity of the 38 kD band, proteins synthesized by yeast were also submitted to Western analysis. Cleared yeast lysates prepared as described above were electrophoresed on polyacrylamide gels (Laemmli, supra) and proteins were subsequently electroblotted onto nitrocellulose filters (Towbin, et. al., *Proc. Natl. Acad. Sci. U.S.A.* 76:3450, 1979). The filter was preincubated for 1 h with 1% (BSA) in PBS and subsequently treated with a monoclonal antibody to *P. vivax* CS protein for 12 h at 4° C. The filters were washed with 1% BSA/PBS and a second goat anti-mouse antibody conjugated with horseradish peroxidase (BioRad Laboratories, Richmond, Calif.) added. Finally, the filters were incubated with horseradish peroxidase color development reagent (Bio-Rad, Richmond, Calif.) and washed. The Western analysis showed that the fusion protein reacted with the monoclonal antibodies. (FIG. 4)

EXAMPLE 2

Purification of the circumsporozoite polypeptide of the *Plasmodium vivax*

The yeast cultures expressing a part of the circumsporozoite polypeptide were prepared as in Example 1. The expressed polypeptide consisted of 234 amino acids including all of the repeat domain and a conserved region, namely Region I of Dame, J. B., et al, *Science* 225:628 (1984). The N-terminal amino acid of the expressed polypeptide is alanine in the nucleotide positions No. 385-7 (GCA) and the C-terminal amino acid is proline at nucleotide positions No. 1084–1086 (CCA); Arnot, et al, *Science* 230:815–818, 1985. The first step of purification of the peptide fragment expressed by yeast consisted of subjecting the extracts to temperatures of 100° C. The purification was performed as follows:

Extracts from pelleted yeast from 20 liters of yeast culture were prepared in a bead beater, diluting the yeast in an equal volume of 0.1M sodium phosphate buffer, pH 7.3, 0.1% Triton-X, 1 mM EDTA, 1 mM PMSF (phenylmethylsulfonylfluoride) and 1 microgram per ml of pepstatin. The extract (370 ml) was added to 200 ml of boiling water containing 1 mM of PMSF and 1 microgram/ml of leupeptin. The mixture was brought to a temperature of 100° C. and kept for ten minutes with constant stirring at this temperature. The mixture was cooled to 0° C. and centrifuged at 18,000 rotations per minute in a Beckman Ultracentrifuge Rotor TI-19, (Beckman Instruments, Palo Alto, Calif.) for fifteen minutes. The supernatant was removed and then lyophilized.

The dry material was dissolved in 120 ml of water, centrifuged to remove a small residual amount of insoluble material, dialyzed extensively against distilled water for 48 hours and lyophilized again. The powder was dissolved in 3 mM sodium potassium phosphate buffer, pH 7.5, and the conductivity adjusted with water to 0.58 mS. The solution was centrifuged to remove insoluble materials and subjected to anion exchange chromatography in a DEAE-Sephacel (Pharmacia Fine Chem Co., Piscataway, N.J.) column (5 cm×24 cm) equilibrated in the same buffer. The flow rate was adjusted to 100 ml per hour and 21 ml per tube were collected. The column was then washed with 500 ml of the same buffer, i.e., with about one column volume. The elution continued with a buffer formed in a linear gradient in which 1,500 ml of the initial buffer were gradually mixed with 1,500 ml of the same buffer also containing 0.75M NaCl. The presence of the circumsporozoite polypeptide in the various fractions eluting from the column was detected using a competitive radioimmunoassay described below.

The positive fractions eluted between fraction Nos. 65–90 in a symmetrical peak with conductivities between 2 and 10 mS (FIG. 5). The full fractions 65–90 were lyophilized, redissolved in 60 ml of 0.3M NaCl and dialyzed against 0.3M NaCl at room temperature for several hours. The dialyzate was centrifuged to remove a small amount of insoluble material and one third, i.e. 20 ml, was subjected to molecular sieve chromatography on Sephadex G-200 (Pharmacia) equilibrated with 0.3M sodium chloride. The Sephadex was superfine and the column was 5 cm in diameter and 100 cm long. Samples of 21 ml per tube were collected from the column. The CS polypeptide eluted in a sharp symmetrical peak between tubes 51-57. However, materials with higher and lower molecular weight in smaller amounts were distributed in tubes preceding and following this peak. The contents of tubes 51-57 were pooled, dialyzed extensively against distilled water, and lyophilized. A total amount of 89 mg of pure circumsporozoite polypeptides were recovered. On this basis, we calculated that the yield from 20 liters of yeast is 89×3, i.e., 267 mg of pure protein or about 13 mg per liter of yeast culture. The purity of the recovered circumsporozoite polypeptide was assessed by sodium dodecyl sulfate polyacrylamide gel electrophoresis (SDS-PAGE) and by isoelectric focusing under denaturing conditions. At concentrations of 2 mg per ml, a single band with an isoelectric point of 4.3 was detected by isoelectric focusing (FIG. 7). By SDS-PAGE, a doublet was detected with a molecular weight between 43,000 and 45,000 (FIG. 6). The extinction coefficient at 280 nanometers of solutions of the CS polypeptide containing 1 mg of protein per ml was 0.2. A sample of the polypeptide was subjected to partial N-terminal sequence analysis and the major sequence was alanine-glutamic acid-proline-lysine-asparagine-proline, as expected. Another sample was radiolabelled with $^{125}I$ and immunoprecipitated with monoclonal antibodies specific to the CS protein of *Plasmodium vivax*. Between 75 and 85% of the counts were specifically recognized by the antibody.

Figure 12:
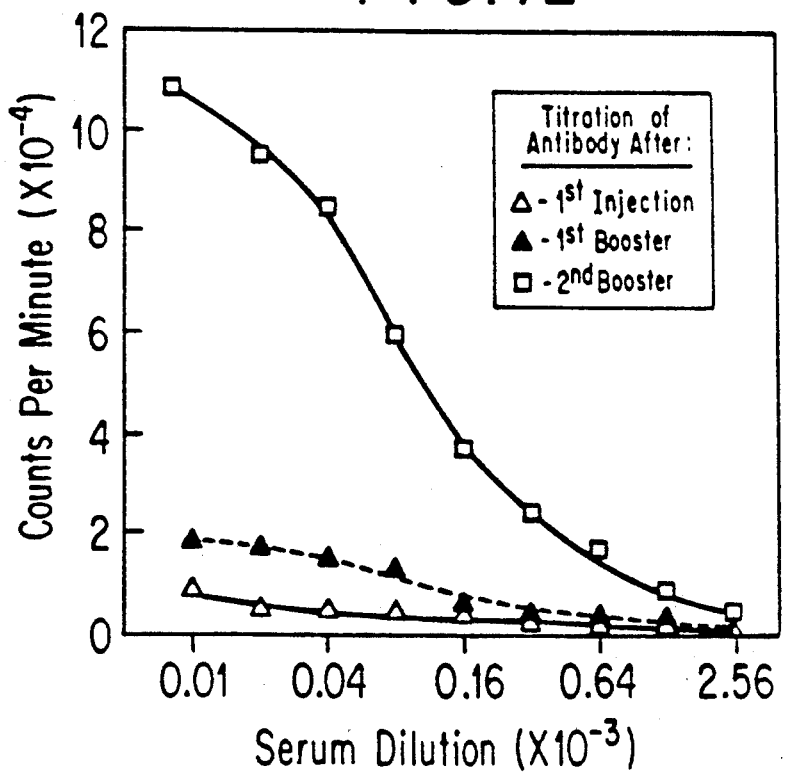
FIG. 12 is a plot of the binding of mouse antisera to immobilized synthetic non-repeat peptide, as a function of the antisera dilution.

A solid state competitive radioimmunoassay was used to detect the engineered CS polypeptide during the purification procedure. The standard curve relating the dose of antigen with the signal obtained in the radioimmunoassay was prepared as follows. The purified, engineered CS polypeptide was radiolabelled with $^{125}I$ to a specific activity of about $2\times10^6$ counts per minute per microgram protein using the well-known iodogen method. Mixtures containing a constant amount of radiolabelled engineered CS polypeptide and variable amounts of purified cold (i.e. unlabeled) engineered CS polypeptide (in a total volume of 100 microliters) were prepared. Thirty microliters of the mixtures were then delivered to the bottom of wells of microtiter plates pre-coated with monoclonal antibodies to the circumsporozoite protein of *Plasmodium vivax* (2F2). This monoclonal antibody reacts with the repetitive epitope of the circumsporozoite protein. (Nardin E. H. et al, J. Exp. Med., 156:20, 1982). The inhibitory effect of the cold peptide on the binding of the labeled peptide to the bottom of the wells was proportional to the concentration of cold peptide. This assay detected concentrations of cold peptide as low as five nanograms per ml (FIG. 8). The assay of the column fractions and of the extracts was performed exactly as described above and the degree of inhibition obtained was referred to the standard curve (FIG. 8) to calculate the concentration of the CS protein peptide. All dilutions and washing in this assay were performed in a phosphate buffer saline (PBS) containing 1.0% bovine serum albumin (BSA) and 0.1% sodium azide.

On the basis of the results of these assays, we calculated that the yeast cultures contain about 60 mg of circumsporozoite protein per liter and that the recovery of the purified material was about 20% of the total. There were no losses in the initial step of purification, i.e., following the boiling of the extracts this step removed more than 90% of the non-relevant protein bands observed in the SDS-PAGE of the original extracts.

EXAMPLE 3

Immunization of mice with the yeast-engineered *P. vivax* polypeptide

The purified engineered CS polypeptide was then used as an antigen to immunize mice. Ten outbred female Swiss-Webster, 8-12 week old mice were injected with 50 micrograms of the purified peptide adsorbed on aluminum hydroxide. Three and six weeks afterwards, the mice were boosted with the same dose of antigen again using aluminum hydroxide as adjuvant. Ten days later, the mice were bled and the sera were subjected to analysis by an immunoradiometric assay to detect antibodies to the CS polypeptide. In this assay, the wells of microtiter plates are coated with purified engineered CS polypeptide (10 micrograms/ml in PBS) and then incubated the wells with 30 microliters of various dilutions of the mouse serum in PBS-BSA. The wells were then washed and re-incubated with 50,000 cpm of radiolabelled affinity-purified goat anti-mouse immunoglobulin ($10^7$ cpm/microgram of protein) diluted in PBS-BSA. The wells were then washed again and counted.

All sera reacted with the engineered CS polypeptide at dilutions of 1:10,000 or greater. The results of a titration of the pooled sera are shown in FIG. 9. That these sera contained large amounts of antibodies to the "repeats" of the *P. vivax* CS protein was shown in two experiments described below.

1) A synthetic 18-amino acid peptide (18-mer) comprising the sequence (Asp-Gly-Gln-Pro-Ala-Gly-Asp-Arg-Ala)$_2$ and representing two tandem repeats of the *P. vivax* CS Protein was synthesized as described in (a) copending U.S. patent application Ser. No. 754,645 filed on Jul. 9, 1985 and incorporated by reference in the present application; and (b) Arnot, et al. Science, 230:815, 1985. This peptide was used to coat wells of microtiter plates and the antibody contents of the sera detected by the immunoradiometric assay described above. All sera reacted with titers at 1:4,000 or above. The results of titrations of pooled sera obtained after the second antigen booster injection are shown in FIG. 10.

2) The synthetic 18-amino acid peptide was also used to inhibit the binding of antibodies, present in the pooled antiserum, to the wells of plastic plates coated with the engineered CS polypeptide. In these experiments, we first incubated samples of a 1:3,000 dilution of the pooled serum from the mice (obtained after the 2nd booster rejection) with increasing concentrations of the 18-amino acid peptide described above. As a control, samples of serum were incubated with the same concentration of another 18-mer peptide with a different and unrelated sequence of amino acids. Following an incubation of one hour at room temperature, 30 microliters of the mixtures were added to wells of plates precoated with the engineered CS polypeptide. The wells were then washed, incubated with radiolabelled goat anti-mouse immunoglobulin, as described above, washed again and counted. The results shown in FIG. 11 demonstrated that the "repeat" peptide (but not the control peptide) inhibited about 50% of the reaction between the antibodies and the CS protein. All dilutions and washings in these experiments were performed with PBS-BSA.

The same sera were also analyzed for the possible presence of antibodies to Region 1 of Dame, et al., supra. For this purpose, we used as an immobilized antigen a small synthetic peptide NH$_2$-Cys-Tyr-Asn-Glu-Lys-Ile-Glu-Arg-Asn-Asn-Lys-Leu-Lys-Gln-Pro-COOH. This peptide includes a sequence of five amino acids which are common to all CS proteins from all malaria parasites examined to date, Lys-Leu-Lys-Gln-Pro (Dame et al., Science, 225:593, 1984, and Enea, V., personal communication). The first two amino acids (Cys and Tyr) are extraneous to the CS protein and were added for purposes of coupling the peptide to a carrier protein and radiolabelling with $^{125}$I. This peptide was used to coat wells of microtiter plates and the antibody contents in the sera were detected as described above. After the second booster, all sera recognized this small peptide at dilutions of 1:2,000 or greater. The results of titrations of a pool of these sera is shown in FIG. 12.

The sera were also tested by indirect immunofluorescence using the sporozoite of *P. vivax* as the antigen. All sera were positive at dilutions of 1:1,000 or greater.

Finally, another experiment demonstrated that relatively low levels of antibodies to the engineered CS protein neutralize the infectivity of *P. vivax* sporozoites. The assay was performed as described in *J. Immunol.* 132:909, 1984 (incorporated by reference) using the human hepatoma cell line Hep 62 as the target of parasite invasion. The results, set forth in Table I, below, show that a significant degree of inhibition was obtained at serum dilutions of 1:5,000. The percentages of inhibitions were calculated as 100-[(mean experimental values/mean of controls)×100]. Controls consisted of sporozoites incubated with equivalent concentrations of normal (pre-immune) mouse serum.

TABLE I

INHIBITION OF P. VIVAX SPOROZOITES INTO HEPATOCYTES IN VITRO BY ANTIBODIES TO THE YEAST-ENGINEERED CS PROTEIN

| (Serum Dilution)$^{-1}$ | % Inhibition |
| --- | --- |
| 50 | 91 |
| 250 | 91 |
| 1,000 | 77 |
| 5,000 | 42 |

What I claimed is:

1. A synthetic peptide consisting essentially of the amino acids KLKQP in sequence, said amino acid sequence being conserved in the CS protein of *Plasmodium knowlesi*, *Plasmodium falciparum* and *Plasmodium vivax*.

2. A synthetic polypeptide amino acid sequence consisting essentially of
  (a) an immunogenic repetitive sequence consisting essentially of DRAD/AGOPAG consecutively occurring at least twice and corresponding to all or part of the repetitive immunodominant epitope region of *P. vivax* circumsporozoite protein; and
  (b) located in at least one of the N- and C-terminal of said repetitive sequence, a non-repetitive terminal of said repetitive sequence, a non-repetitive amino acid sequence KLKQP which in the native circumsporozoite protein (1) immediately precedes or follows the repetitive immunodominant epitope region of said protein, and (2) is conserved among different malarial species.

3. The polypeptide of claim 2 wherein said sequence KLKQP in (b) is located at the N-terminal of said polypeptide and is the non-repetitive conserved sequence immediately preceding the repetitive epitope region of the native circumsporozoite protein and located proximal to the N-terminal of said protein.

* * * * *